United States Patent
Feng et al.

(10) Patent No.: US 10,278,727 B2
(45) Date of Patent: May 7, 2019

(54) PERICARDIUM PUNCTURE NEEDLE ASSEMBLY

(71) Applicant: SYNAPTIC MEDICAL (BEIJING) CO. LTD., Beijing (CN)

(72) Inventors: Ji Feng, Beijing (CN); Jie Gong, Beijing (CN); Xin Hua, Beijing (CN); Chang-sheng Ma, Beijing (CN); Sophia Wang Hansen, Beijing (CN)

(73) Assignee: Synaptic Medical (Beijing) Co. Ltd., Beijing (CN)

( * ) Notice: Subject to any disclaimer, the term of this patent is extended or adjusted under 35 U.S.C. 154(b) by 401 days.

(21) Appl. No.: 14/758,191

(22) PCT Filed: Dec. 27, 2013

(86) PCT No.: PCT/CN2013/001652
§ 371 (c)(1),
(2) Date: Jun. 26, 2015

(87) PCT Pub. No.: WO2014/101298
PCT Pub. Date: Jul. 3, 2014

(65) Prior Publication Data
US 2015/0359561 A1   Dec. 17, 2015

(30) Foreign Application Priority Data

Dec. 28, 2012 (CN) .......................... 2012 1 0582505
Jul. 17, 2013 (CN) .......................... 2013 1 0298360

(51) Int. Cl.
*A61B 17/00* (2006.01)
*A61B 17/34* (2006.01)

(52) U.S. Cl.
CPC ...... *A61B 17/3417* (2013.01); *A61B 17/3478* (2013.01); *A61B 2017/00247* (2013.01)

(58) Field of Classification Search
CPC ............ A61B 17/3417; A61B 17/3478; A61B 2017/00247
See application file for complete search history.

(56) References Cited

U.S. PATENT DOCUMENTS 4,991,578 A * 2/1991 Cohen .................. A61N 1/0587
607/2
5,827,216 A * 10/1998 Igo .................... A61B 17/00234
604/176

(Continued)

FOREIGN PATENT DOCUMENTS

CN        2621615 Y      6/2004
CN      102100575 A      6/2011

(Continued)

OTHER PUBLICATIONS

International Search Report dated Apr. 3, 2014 in regard to International Application No. PCT/CN2013/001652.

(Continued)

*Primary Examiner* — Julie A Szpira
(74) *Attorney, Agent, or Firm* — Knobbe, Martens, Olson & Bear, LLP (57) ABSTRACT

A pericardium puncture needle assembly comprises a puncture needle (12) and a guide wire (13) capable of sliding in the puncture needle (12); or comprises an outer sleeve (22) and a guide wire (13) capable of sliding in the outer sleeve (22); or comprises an outer sleeve (22) and a puncture needle (12) and a guide wire (13) capable of sliding in the outer sleeve (22), wherein after the puncture needle (12) is pulled out of the outer sleeve (22), the guide wire (13) is capable of sliding in the outer sleeve (22). The guide wire (13) is made of a highly elastic material and comprises a far-end bent segment (32). The far-end bent segment (32) is formed by bending the guide wire (13) and has a preset bending shape, and is suitable for being recovered from a stretching (Continued)

state to the preset bending shape. The tip of the far-end bent segment has a pointed structure. The pointed structure has a far end and a near end, the far-end has a pointed end for puncturing, and the pointed end rotates by an angle of at least 90 degrees relative to the near end of the pointed structure on a length not more than 3 mm of the pointed structure. The puncturing direction of the guide wire (13) falls in a plane defined by a normal direction of a needle point plane of the puncture needle (12) or the outer sleeve (22) and an axial line of the puncture needle (12) or the outer sleeve (22). When the pericardium puncture needle assembly is used for puncturing pericardium, the degree of twisting freedom of the guide wire (13) can be limited to some extent.

26 Claims, 4 Drawing Sheets

(56) References Cited

U.S. PATENT DOCUMENTS

| | | | | |
|---|---|---|---|---|
| 5,972,013 | A * | 10/1999 | Schmidt | A61B 17/3417 604/164.01 |
| 7,666,203 | B2 * | 2/2010 | Chanduszko | A61B 17/0057 128/898 |
| 7,824,403 | B2 * | 11/2010 | Vaska | A61B 17/2202 33/512 |
| 2003/0114796 | A1 | 6/2003 | Schmidt | |
| 2004/0167558 | A1 | 8/2004 | Igo et al. | |
| 2005/0101984 | A1 * | 5/2005 | Chanduszko | A61B 17/0057 606/185 |
| 2005/0245876 | A1 * | 11/2005 | Khosravi | A61B 17/00491 604/164.1 |
| 2006/0247672 | A1 * | 11/2006 | Vidlund | A61B 17/3421 606/190 |
| 2007/0005019 | A1 * | 1/2007 | Okishige | A61B 17/3478 604/175 |
| 2009/0105654 | A1 | 4/2009 | Kurth et al. | |
| 2012/0095434 | A1 * | 4/2012 | Fung | A61B 17/3421 604/500 |
| 2014/0094836 | A1 * | 4/2014 | Feng | A61B 17/3478 606/185 |

FOREIGN PATENT DOCUMENTS

| | | |
|---|---|---|
| CN | 102793577 A | 11/2012 |
| EP | 1 852 075 | 11/2007 |
| WO | WO 2012/163083 | 12/2012 |

OTHER PUBLICATIONS

European Search Report dated Aug. 11, 2016 in corresponding European Patent Application No. 13868498.0 (7 pages).

* cited by examiner

PERICARDIUM PUNCTURE NEEDLE ASSEMBLY

CROSS REFERENCE TO RELATED APPLICATIONS

This application is a national phase of international Application No. PCT/CN2013/001652 filed on Dec. 2, 2013 which claims priority to Chinese patent application 201210582505.4 filed on Dec. 28, 2012 and Chinese patent application 201310298360.X filed on Jul. 17, 2013, the entire disclosure of which is incorporated herein by reference.

FIELD OF THE INVENTION

The present invention relates to a puncture needle assembly, and more particularly, it relates to a pericardium puncture needle assembly.

BACKGROUND OF THE INVENTION

Pericardium is a layer of connective tissue membrane that tightly wraps around the heart. In epicardial ablation, it is necessary to manually open a path through the pericardium tightly around the heart, in order to let the ablation device to access the space between the pericardium and the outwall of heart to conduct ablation.

There are a great diversity of pericardium puncture equipments on market. For example, Chinese patent CN00257117.X disclosed a type of noninvasive pericardium puncture needle, which comprises an outer sheath, an inner needle, and an end cap. The outer sheath is a flexible hollow tube that accommodates the inner needle. The inner needle is a solid puncture needle, which is fixed to the distal end of the outer sheath by the end cap. Once the pericardium is pierced by the needle, the needle is then withdrawn. The outer sheath continues advancing into the pericardium, so that the pericardial effusion can be extracted or drugs can be injected.

However, in clinical operations, the existing puncture needles often pierce insufficiently and lead to puncture failure.

SUMMARY OF THE INVENTION

A pericardium puncture needle assembly, characterized in comprising a puncture needle and a guide wire, wherein the guide wire can slide in the puncture needle, and the guide wire is made of a high elastic material; the guide wire comprises a distal end bent section, the distal end bent section is formed by bending the guide wire and has a preset bent shape, and the distal end bent section is adapted to regain the preset bent shape from a straightened state, and its tip end part is of a sharp tip structure; the sharp tip structure is provided with a distal end and a proximal end, the distal end of the sharp tip structure is provided with a sharp tip end for puncturing, and within a length not larger than 3 mm of the sharp tip structure, the rotation angle of the sharp tip end relative to the proximal end of the sharp tip structure is at least 90 degree; the puncturing direction of the guide wire is located in a plane defined by the normal direction of the needle point plane of the puncture needle and the axial line of the puncture needle.

A pericardium puncture needle assembly, characterized in comprising an outer sheath and a guide wire, wherein the guide wire can slide in the outer sheath, and the guide wire is made of a high elastic material; the guide wire comprises a distal end bent section, the distal end bent section is formed by bending the guide wire and has a preset bent shape, and the distal end bent section is adapted to regain the preset bent shape from a straightened state, and its tip end part is of a sharp tip structure; the sharp tip structure is provided with a distal end and a proximal end, the distal end of the sharp tip structure is provided with a sharp tip end for puncturing, and within a length not larger than 3 mm of the sharp tip structure, the rotation angle of the sharp tip end relative to the proximal end of the sharp tip structure is at least 90 degree; the puncturing direction of the guide wire is located in a plane defined by the normal direction of the needle point plane of the outer sheath and the axial line of the outer sheath.

A pericardium puncture needle assembly, characterized in comprising an outer sheath, a puncture needle and a guide wire, wherein the puncture needle can slide in the outer sheath, and when the puncture needle is pulled out of the outer sheath, the guide wire can slide in the outer sheath, and the guide wire is made of a high elastic material; the guide wire comprises a distal end bent section, the distal end bent section is formed by bending the guide wire and has a preset bent shape, and the distal end bent section is adapted to regain the preset bent shape from a straightened state, and its tip end part is of a sharp tip structure; the sharp tip structure is provided with a distal end and a proximal end, the distal end of the sharp tip structure is provided with a sharp tip end for puncturing, and within a length not larger than 3 mm of the sharp tip structure, the rotation angle of the sharp tip end relative to the proximal end of the sharp tip structure is at least 90 degree; the puncturing direction of the guide wire is located in a plane defined by the normal direction of the needle point plane of the outer sheath and the axial line of the outer sheath.

In a specific implementation of the present invention, the puncturing direction of the guide wire is in the normal direction of the needle point plane of the puncture needle or the outer sheath.

In a specific implementation of the present invention, the distal end of the puncture needle or the outer sheath comprises a distal end bent section, the axial line or the center line of the distal end bent section of the guide wire is located in a plane, and the axial line or the center line of the distal end bent section of the puncture needle or the outer sheath is located in a plane.

In a specific implementation of the present invention, the guide wire comprises a proximal end bent section, the outer sheath is further provided with an inner sheath, and the proximal end of the inner sheath comprises a bent section; the length between the proximal end bent section of the guide wire and the sharp tip end of the guide wire is L, and the length L is larger than 80 mm.

In a specific implementation of the present invention, the curvature radius of the proximal end bent section of the guide wire is selected such that within a length range of not larger than 20 mm, the rotation angle of the proximal end bent section of the guide wire is larger than 15 degree and is preferably 15-90 degree; the curvature radius of the proximal end bent section of the inner sheath is selected such that within a length range of not larger than 20 mm, the rotation angle of the proximal end bent section of the inner sheath is larger than 45 degree and is preferably 45-90 degree.

In a specific implementation of the present invention, the normal direction of the needle point plane of the outer sheath and the axial line of the pipe body of the outer sheath define a plane A, the axial line or the center line of the proximal end bent section of the inner sheath is located in the same plane B, and an included angle α is formed between the plane A and the plane B; the axial line or the center line of the proximal end bent section of the guide wire is located in the same plane C, and an included angle β is formed between the plane C and a plane D where the axial line or the center line of the distal end bent section of the guide wire is located; the included angle β is equal to the included angle α; preferably, both of the included angle α and the included angle β are 180 degree.

In a specific implementation of the present invention, the internal structure of the puncture needle is of a non-revolution body structure, and the guide wire is of a non-revolution body structure.

In a specific implementation of the present invention, a guide wire positioner is provided at the proximal end of the guide wire, and the cross section of the guide wire positioner is of a non-revolution body structure.

In a specific implementation of the present invention, the outer sheath is further provided with an inner sheath, the inner sheath can freely slide in the outer sheath, and the guide wire extends in the inner sheath; preferably, the end face of the distal end port of the inner sheath and the end face of the distal end port of the outer sheath are located in the same plane; more preferably, the distal end of the outer sheath is of a blunt end structure.

In a specific implementation of the present invention, the guide wire positioner is removably fixed on the guide wire; when the guide wire is propelled forwardly, the guide wire positioner is clamped and fixed at the proximal end of the outer sheath; preferably, a joint is fixed at the proximal end of the outer sheath, the proximal end of the joint is provided with a groove matched with the shape of the distal end of the guide wire positioner, and the guide wire positioner can be clamped and fixed at the proximal end of the joint; preferably, after the guide wire positioner is clamped and fixed at the proximal end of the outer sheath, the sharp tip structure of the distal end of the guide wire extends to the outside of the outer sheath.

In a specific implementation of the present invention, an included angle α is formed between the plane where the axial line or the center line of the distal end bend section of the guide wire is located and the normal direction of the end face of the distal end port of the outer sheath, wherein the included angle α is 0 or 180 degree.

In a specific implementation of the present invention, a negative pressure device is fixed at the proximal end of the puncture needle or the outer sheath.

In a specific implementation of the present invention, a flexible element, which is made of a high molecular material, is provided at the distal end of the puncture needle or the outer sheath.

In a preferable implementation of the present invention, when the pericardium puncture needle assembly is penetrating the pericardium, the torsional freedom of the guide wire may be limited to some extent.

DETAILED DESCRIPTION OF THE EMBODIMENTS

A further detailed description of the technical solutions of the present invention will be given below by means of embodiments in combination with the accompanying drawings. However, the present invention is not merely limited to the following embodiments. When describing the distal end and the proximal end of a component, in general, the distal end refers to the end of the component close to the puncturing part of a puncture needle assembly, and the proximal end refers to the end of the component close to the handle part or the operating part of the puncture needle assembly.

Figure 1:
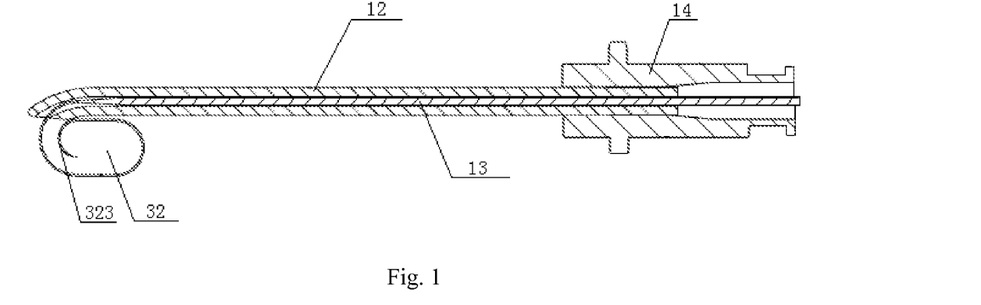
FIG. 1 is a schematic diagram of a structure of a pericardium puncture needle assembly according to a specific implementation of the present invention.

FIG. 1 is a schematic diagram of the structure of a pericardium puncture needle assembly according to a specific implementation of the present invention. The pericardium puncture needle assembly includes a puncture needle 12, and a guide wire 13 extends in the puncture needle 12. The guide wire 13 is of a slender and bendable flexible structure and includes a distal end bent section 32. The distal end bent section 32 of the guide wire 13 is formed by bending the guide wire 13 and has a distal end and a proximal end. The tip end part (i.e., the distal end part) of the distal end bent section 32 is of a sharp tip structure, and the proximal end is connected with the rest part of the guide wire 13. The guide wire 13 is made of a high elastic material. The distal end bent section has a preset bent shape, and due to the flexibility, the distal end bent section can enter into a straightened state under the action of an external force (for example, when being located in the puncture needle or an outer sheath) and is adapted to regain the preset bent shape from the straightened state after the external force is removed (for example, after penetrating through the puncture needle or the outer sheath). The distal end bent section 32 and the guide wire 13 can be integrally formed, or can be separately formed and connected together. The guide wire 13 can be of a solid structure and no hollow cavity is provided therein, or the guide wire 13 can be of other proper structures.

Within a length range not larger than 3 mm beginning from the sharp tip end of the distal end bent section of the guide wire, the rotation angle of the sharp tip end is at least 90 degree (namely, on a length not larger than 3 mm of the sharp tip structure, the rotation angle of the sharp tip end relative to the proximal end of the sharp tip structure is at least 90 degree). Preferably, within a length range of 1-2 mm beginning from the sharp tip end of the distal end bent section of the guide wire, the rotation angle of the sharp tip end is at least 90 degree.

After the sharp tip end of the guide wire penetrates through the pericardium, the angle between the orientation of the sharp tip end and the advancing direction of the guide wire is larger than 90 degree, thus the pericardium is unlikely to be hurt. In the present invention, the sharp tip structure refers to a structure formed by a part of the guide wire within the length range not larger than 3 mm beginning from the sharp tip end by rotating the sharp tip end of the guide wire at least 90 degree, and the minimal curvature radius of the sharp tip structure is not larger than 0.1 mm. That is to say, the sharp tip structure of the tip end part of the distal end bent section of the guide wire is provided with a distal end and a proximal end, wherein the distal end of the sharp tip structure is provided with a sharp tip end, and the proximal end of the sharp tip structure is connected with the rest part of the distal end bent section. The rotation angle of the axial line of the sharp tip end of the sharp tip structure relative to the normal direction of the cross-section of the proximal end of the sharp tip structure is at least 90 degree. In an implementation, the length of the sharp tip structure is not larger than 3 mm. In a preferable implementation, the length range of the sharp tip structure is 1-2 mm. In the present invention, the sharp tip end refers to the tip end of the distal end of the sharp tip structure, which is very sharp and can be of a micro spherical structure.

As shown in FIG. 1, after the sharp tip end rotates 90 degree, the bend of the distal end bent section 32 extending from the proximal end of the sharp tip structure to the proximal end of the distal end bent section 32 can be in the shape of a spiral line or an involute and can also be other proper irregular bends, such as a combination of a circular arc and a straight line, a combination of an involute and a straight line or other proper bends. When the bend of the distal end bent section 32 extending from the proximal end of the sharp tip structure to the proximal end of the distal end bent section 32 is in the shape of the spiral line or the involute, the curvature radius thereof can increase gradually or increase step by step. When the bend of the distal end bent section 32 extending from the proximal end of the sharp tip structure to the proximal end of the distal end bent section 32 is an irregular bend, such as the combination of the circular arc and the straight line, the combination of the involute and the straight line or other proper bends, the curvature radius thereof can also change irregularly. For example, the curvature radius thereof increase gradually or increase step by step, but with the further bending of the guide wire, the curvature radius thereof starts to become small and then gradually increases or increases step by step.

After the distal end of the distal end bent section 32 penetrates the pericardium, since the distal end is adapted to regain the preset bent shape from the straightened state, the angle between the orientation of the sharp tip end and the advancing direction of the guide wire is larger than 90 degree, and thus the heart will not be punctured. Even if the distal end bent section 32 gradually enters the pericardium, and the angle between the orientation of the sharp tip end and the advancing direction of the guide wire may become smaller than 90 degree due to the action of the external force, the heart is unlikely to be hurt, because at this time, the guide wire is long and flexible, and thus the force acted on the guide wire cannot be transmitted to the sharp tip end. In addition, the sharp tip end is within the three-dimensional enclosure of the bent shape of the distal end bent section, and thus the pericardium is unlikely to be hurt during puncture. Even if the sharp tip end is beyond the three-dimensional enclosure of the bent shape of the distal end bent section, since the guide wire is long and flexible, the force acted on the guide wire cannot be transmitted to the sharp tip end, and therefore the heart is unlikely to be hurt. Within a length range not larger than 3 mm beginning from the sharp tip end, the sharp tip structure includes a bent section 323, and the curvature radius thereof is not larger than 2 mm.

The puncture needle 12 is of a tubular structure, includes a distal end and a proximal end and can be made of any proper biocompatible material, such as stainless steel material or nickel-titanium alloy material. The pipe body of the puncture needle 12 can be consisted of a section of pipe and can also be consisted of two sections of pipes. The distal end of the puncture needle 12 can further include a distal end bent section (not shown in the figure). The distal end of the puncture needle 12 can be of a structure without a needle point, for example, a blunt end structure, thus avoiding hurt to the internal organs during puncture, and ensuring that the blunt end structure abuts the pericardium during puncture of the guide wire 13 in the puncture needle 12, so as not to hurt the heart or the pericardium. The distal end of the puncture needle 12 can also be of a structure with a needle point.

According to a preferred embodiment of the present invention, when the pericardium puncture needle assembly is in use, the distal end bent section of the guide wire 13 is located in a plane, and the distal end bent section of the puncture needle 12 is located in a plane (namely, the axial line or the center line of the distal end bent section of the guide wire 13 is located in a plane, and the axial line or the center line of the distal end bent section of the puncture needle 12 is located in a plane). Due to such a structure of the guide wire and the puncture needle, the flexible guide wire 13 can be automatically rotated and located in the puncture needle 12 easily, such that the puncturing direction of the guide wire can be automatically adjusted. When the distal end bent section 32 is entirely located in the puncture needle 12, the distal end bent section 32 is at the straightened state. When the guide wire 13 is propelled forwardly, the sharp tip end of the distal end bent section 32 extends out from the pipe body of the puncture needle 12. The sharp tip end punctures the pericardium, the guide wire 13 gradually enters into the pericardium, during the process the part of the distal end bent section 32 entered into the pericardium begins to gradually bend until regaining the preset shape, and the puncture is finished.

Figure 2:
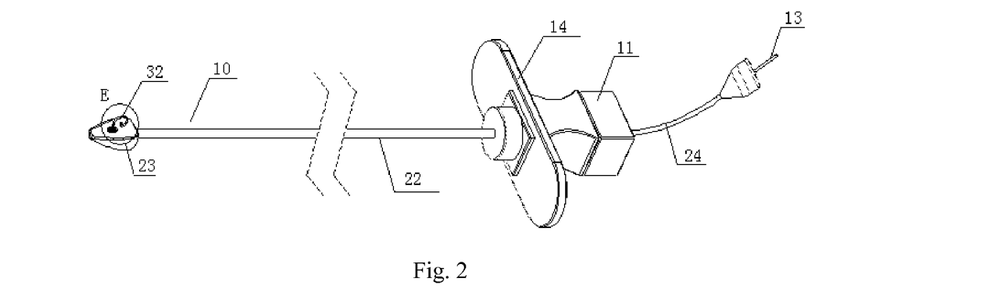
FIG. 2 is a schematic diagram of a three-dimensional structure of a pericardium puncture needle assembly according to a specific implementation of the present invention.
Figure 3:
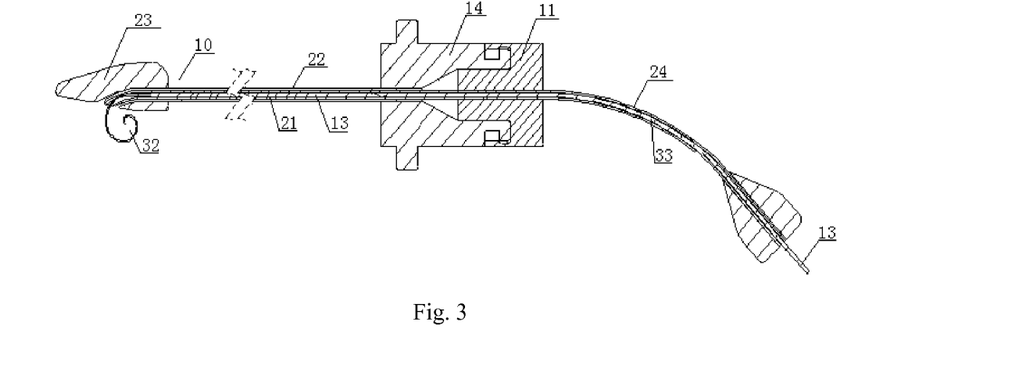
FIG. 3 is a sectional view of the pericardium puncture needle assembly shown in FIG. 2 and shows the internal structures of the pericardium puncture needle assembly of a preferred embodiment of the present invention.

FIG. 2 is a schematic diagram of a three-dimensional structure of a preferred pericardium puncture needle assembly 10 of the present invention; FIG. 3 is a sectional view of a pericardium puncture needle assembly 10 according to a preferred embodiment of the present invention and indicates the connection relationship of a joint 11, an outer sheath 22 and the guide wire 13. The outer sheath 22 is of a tubular structure, includes a distal end and a proximal end and can be made of any proper biocompatible material, for example, stainless steel material or nickel-titanium alloy material. The pipe body of the outer sheath 22 can be consisted of a section of pipe and can also be consisted of two sections of pipes. According to a preferred implementation of the present invention, an inner sheath 21 can also be provided in the outer sheath 22, as shown in FIG. 3; the inner sheath 21 can freely slide in the outer sheath 22. The proximal end of the inner sheath 21 can further include a bent section 24, the curvature radius of the bent section 24 is selected such that within a length range not larger than 20 mm, the rotation angle of the bent section 24 is larger than 45 degree, and preferably, within the length range not larger than 20 mm, the rotation angle of the bent section 24 is 45-90 degree. The joint 11 is fixed at the proximal end of the inner sheath 21, and a joint 14 is fixed at the proximal end of the outer sheath 22. The joint 11 and the joint 14 can be Luer joints. Due to the cooperation of the joint 11 and the joint 14, the inner sheath 23 can be prevented from penetrating through the outer sheath 22 to puncture the heart. Alternatively, no inner sheath is arranged in the outer sheath 22, and under this condition, the proximal end of the outer sheath 22 includes a bent section. The distal end of the outer sheath 22 can further include a distal end bent section (not shown in the figure). The distal end of the outer sheath 22 can be of a structure without a needle point, for example, a blunt end structure, thus avoiding hurt to the internal organs during puncture, and ensuring that the blunt end structure abuts the pericardium during puncture of the guide wire 13 in the outer sheath 22, so as not to hurt the heart or the pericardium. The distal end of the outer sheath 22 can also be of a structure with a needle point. Or, a flexible element 23 is arranged at the distal end of the outer sheath 22, and the flexible element 23 is made of a high molecular material, for example, silica gel or other proper materials. In a puncture process, the flexible element 23 can prevent the puncture needle from puncturing the internal organs and can increase the contact surface area of the puncture needle and tissues to ensure better abutment. A flexible element fixing structure (not shown in the figure) can also be arranged at the distal end of the outer sheath 22 for installing the flexible element 23, the installation manner can be welding or adhering, and in this way, when being inserted onto the outer sheath 22, the flexible element 23 is unlikely to twist or drop.

Figure 4:
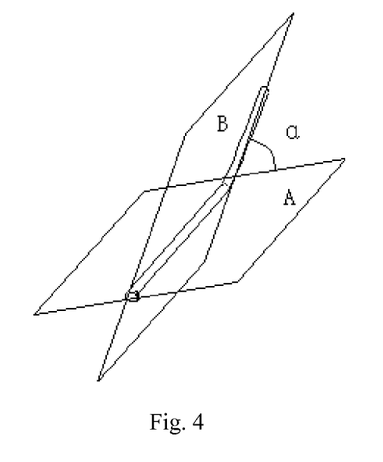
FIG. 4 is a structure diagram of an inner sheath in a pericardium puncture needle assembly of a preferred embodiment of the present invention.

FIG. 4 is a structure diagram of an inner sheath in a pericardium puncture needle assembly of a preferred embodiment of the present invention; and as shown in FIG. 4, the normal direction of the needle point plane of the outer sheath 22 and the axial line or the center line of the pipe body of the outer sheath 22 define a plane A, and the axial line or the center line of the bent section 24 of the proximal end of the inner sheath 21 is located in a plane B. The included angle between the plane A and the plane B is a, and the included angle α is 0-360 degree; and preferably, the included angle α is 180 degree. The needle point plane refers to the section of the outer sheath 22 abutting the tissues, namely, the end face of the outer sheath 22.

Figure 5:
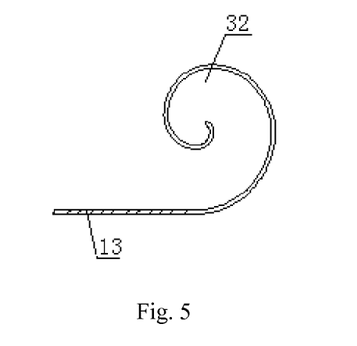
FIG. 5 is an enlarged view of E portion in FIG. 2 and shows the structure of a distal end bent section of a pericardium puncture needle assembly of a preferred embodiment of the present invention.

FIG. 5 is an enlarged view of C portion in FIG. 2 and indicates a structure of a distal end bent section of a guide wire 13 of a pericardium puncture needle assembly of an implementation of the present invention. As shown in FIG. 3 and FIG. 5, the guide wire 13 is of a slender and bendable flexible structure and can be made of any proper high elastic material, for example, nickel-titanium alloy material. The guide wire 13 includes a distal end bent section 32 and a proximal end bent section 33. The distal end bent section 32 and the proximal end bent section 33 are formed by bending the guide wire. The structure of the distal end bent section 32 is a structure adapted to regain the preset bent shape from a straightened state. Since the guide wire is made of the high elastic material, the distal end bent section 32 is at the straightened state when being located in the outer sheath 22 and can regain the preset bent shape after penetrating through the outer sheath 22.

Figure 6:
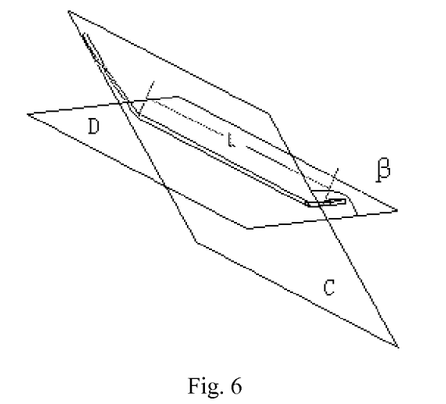
FIG. 6 is a structure diagram of a guide wire in a pericardium puncture needle assembly of a preferred embodiment of the present invention.

FIG. 6 is a structure diagram of a guide wire in a pericardium puncture needle assembly of a preferred embodiment of the present invention. As shown in FIG. 6, the length between the proximal end bent section 33 of the guide wire 13 and the sharp tip end of the guide wire 13 is L, namely, when the guide wire 13 is in the straightened state, in the area spacing a length of L from the sharp tip end, the proximal end bent section 33 is provided. The length L is larger than 80 mm. The curvature radius of the proximal end bent section 33 is selected such that within a length range not larger than 20 mm, the rotation angle of the proximal end bent section 33 (i.e., the included angle between the axial lines of the two end parts of the proximal end bent section 33) is larger than 15 degree, and preferably, within the length range not larger than 20 mm, the rotation angle of the proximal end bent section 33 (i.e., the included angle between the axial lines of the two end parts of the proximal end bent section 33) is 15-90 degree. The curvature radius of all points of the proximal end bent section 33 are located in the same plane C (i.e., the plane where the axial line of the proximal end bent section 33 is located is the plane C), the included angle between the plane C and a plane D where the distal end bent section 32 of the guide wire 13 is located (i.e., the plane where the axial line of the distal end bent section 33 is located is the plane D) is β, and the included angle β is 0-360 degree; the included angle β is equal to the included angle α; and preferably, the included angle β is 180 degree. In this way, in a puncture process, the torsional freedom of the guide wire can be limited to some extent.

As shown in FIG. 2, FIG. 3 and FIG. 5, after the sharp tip end rotates 90 degree, the bend of the distal end bent section 32 extending from the proximal end of the sharp tip structure to the proximal end of the distal end bent section 32 can be in the shape of a spiral line or in the shape of an involute or can be other proper irregular bends.

According to a preferred embodiment of the present invention, when the pericardium puncture needle assembly is in use, the puncturing direction of the guide wire is located in a plane A defined by the normal direction of the needle point plane of the outer sheath 22 and the axial line of the pipe body of the outer sheath 22. Preferably, the puncturing direction of the guide wire is in the normal direction of the needle point plane of the outer sheath 22. When the distal end bent section 32 is entirely located in the outer sheath 22, the distal end bent section 32 is at the straightened state. When the guide wire 13 is propelled forwardly, the sharp tip end of the distal end bent section 32 extends out from the pipe body of the outer sheath 22. The sharp tip end punctures the pericardium, the guide wire 13 gradually enters into the pericardium, the part of the distal end bent section 32 entered into the pericardium begins to gradually bend until regaining the preset shape, and the puncture is finished. In the implementations as shown in FIG. 2 to FIG. 6, the rest of the structure of the guide wire 13 is the same as that in the implementation as shown in FIG. 1.

Figure 7:
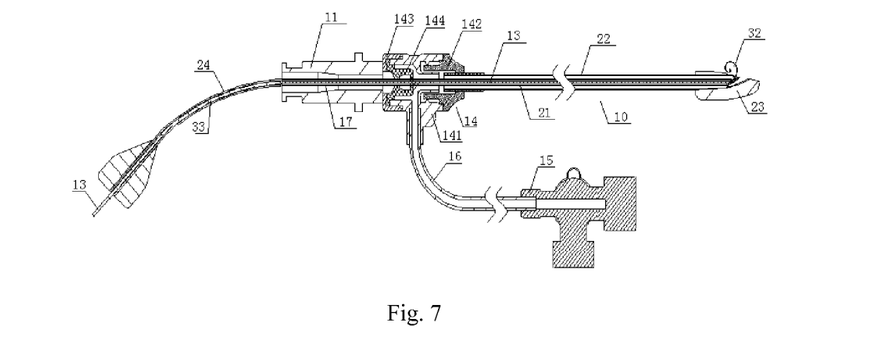
FIG. 7 is a schematic diagram of a structure of a pericardium puncture needle assembly 10 according to another implementation of the present invention.

FIG. 7 is a schematic diagram of a structure of a pericardium puncture needle assembly 10 according to another implementation of the present invention. As shown in FIG. 7, the pericardium puncture needle assembly 10 includes an outer sheath 22, and a guide wire 13 extends in the outer sheath 22. An inner sheath 21 can be provided in the outer sheath 22 or there is no inner sheath provided in the outer sheath. The guide wire 13 is of a slender and bendable flexible structure and includes a distal end and a proximal end. The guide wire 13 includes a distal end bent section 32 and a proximal end bent section 33, and the tip end part of the distal end bent section 32 is of a sharp tip structure. A negative pressure device is further fixed at the proximal end of the outer sheath 22, a flexible element 23 can be arranged at the distal end of the outer sheath 22, and the flexible element 23 is made of a high molecular material, for example, silica gel or other proper materials. In a puncture process, the flexible element 23 can prevent the outer sheath from puncturing the internal organs and can increase the contact surface area of the outer sheath and tissues to ensure better abutment, and a certain absorbing area can be formed between the distal end of the outer sheath 22 and the tissues to generate a negative pressure.

The guide wire 13 is made of a high elastic material, the distal end bent section 32 is formed by bending the guide wire 13, and the structure of the distal end bent section 32 is a structure adapted to regain a preset bent shape from a straightened state. The sharp tip structure of the distal end bent section 32 is provided with a sharp tip end at the distal end. Within a length range not larger than 3 mm extending from the sharp tip end of the sharp tip structure to the proximal end of the sharp tip structure at the distal end bent section of the guide wire, the rotation angle of the sharp tip end relative to the proximal end of the sharp tip structure is at least 90 degree (i.e., the included angle between the orientation or the axial direction of the sharp tip end relative to the normal direction of the lateral section of the proximal end of the sharp tip structure is at least 90 degree). After the sharp tip end rotates 90 degree, beginning from the proximal end of the sharp tip structure, the distal end bent section 32 can be in the shape of an involute, for example, a square involute, a triangular involute or other involute, and the curvature radius thereof continuously increases or increases step by step, as shown in FIG. 7.

In the implementation, the normal direction of the needle point plane of the outer sheath 22 and the axial line of the pipe body of the outer sheath 22 define a plane A, the curvature radius of the proximal end bent section 24 of the inner sheath 21 is located in the same plane B (i.e., the plane where the axial line or the center line of the bent section 24 is located is the plane B), the included angle between the plane A and the plane B is α, and the included angle α is 0-360 degree; and preferably, the included angle α is 180 degree, similarly as shown in FIG. 5.

The length between the proximal end bent section 33 of the guide wire 13 and the sharp tip end of the guide wire 13 is L, namely, when the guide wire 13 is in the straightened state, in the area spacing a length of L from the sharp tip end, the proximal end bent section 33 is provided. The curvature radius of all points of the proximal end bent section 33 is located in the same plane C (i.e., the plane where the axial line or the center line of the proximal end bent section 33 is located is the plane C), the included angle between the plane C and a plane D where the distal end bent section 32 of the guide wire 13 is located is β, and the included angle β is 0-360 degree; the included angle β is equal to the included angle α; and preferably, the included angle β is 180 degree.

In this way, in a puncture process, the torsional freedom of the guide wire can be limited to some extent, similarly as shown in FIG. 6. The negative pressure device includes a connecting valve 14 and a negative pressure tee 15, and the connecting valve 14 is connected with the negative pressure tee 15 through a negative pressure connecting pipe 16. The connecting valve 14 can be integrally formed or can be separately formed, and as shown in FIG. 7, the connecting valve 14 includes a valve body 141 which is provided with a distal end, a proximal end and a central chamber. A lower end cover 142 is arranged at the distal end of the valve body 141, and an upper end cover 143 is arranged at the proximal end of the valve body 141. The proximal end of the outer sheath 22 is fixed in the lower end cover 142, and a section of protective pipe can also be sleeved on the end part of the outer sheath 22. A sealing fin 144 is further arranged in the upper end cover 143 for sealing. One end of the negative pressure connecting pipe 16 is fixed on the connecting valve 14, and the other end of the negative pressure connecting pipe 16 is fixed on the negative pressure tee 15. A joint 11 is further connected to the proximal end of the inner sheath 21, and the joint can be a Luer joint.

According to a preferred embodiment of the present invention, when the pericardium puncture needle assembly is in use, firstly a negative pressure source is turned on, and after absorbing the pericardium onto the flexible element, the puncturing process is started. The puncturing direction of the guide wire 13 is in a plane defined by the normal direction of the needle point plane of the outer sheath 22 and the axial line of the pipe body of the outer sheath 22. Preferably, the puncturing direction of the guide wire 13 is in the normal direction of the needle point plane of the outer sheath 22. When the distal end bent section 32 is entirely located in the outer sheath 22, the distal end bent section 32 is in the straightened state. When the guide wire 13 is propelled forwardly, the sharp tip end of the distal end bent section 32 extends out from the pipe body of the outer sheath 22 and is located in the plane A. The sharp tip end punctures the pericardium, the guide wire 13 gradually enters into the pericardium, the part of the distal end bent section 32 entered into the pericardium begins to gradually bend until regaining the preset shape, and the puncture is finished.

In the implementation as shown in FIG. 7, the rest of the structures of the guide wire 13 are the same as those in the implementation as shown in FIG. 1, and the rest of the structures of the outer sheath 22 are the same as those in the implementations as shown in FIG. 2 to FIG. 6.

Figure 8:
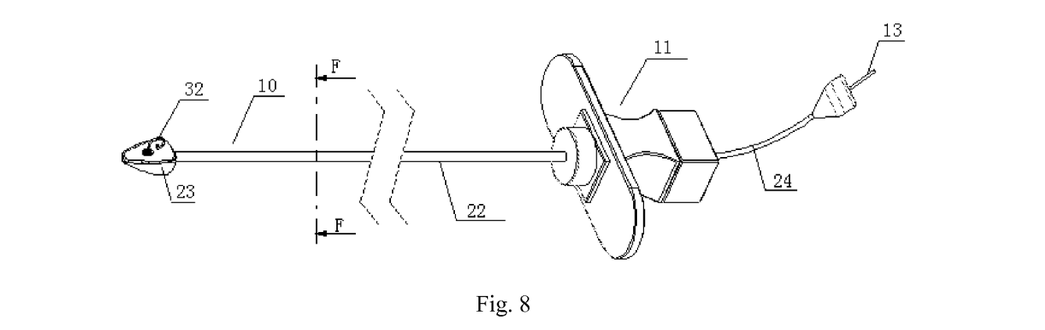
FIG. 8 is a schematic diagram of a structure of a pericardium puncture needle assembly 10 according to another implementation of the present invention.
Figure 9:
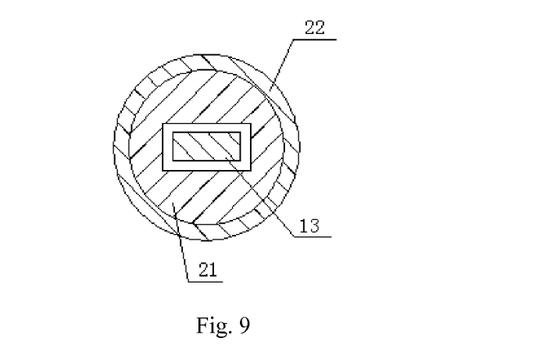
FIG. 9 is a schematic diagram of a cross section along the F-F line in FIG. 8.

FIG. 8 is a schematic diagram of a cross section of a pericardium puncture needle assembly 10 according to another implementation of the present invention; and FIG. 9 is a schematic diagram of a cross section along the F-F line in FIG. 8. As shown in FIG. 8 and FIG. 9, the pericardium puncture needle assembly 10 includes an outer sheath 22, and a guide wire 13 extends in the outer sheath 22. An inner sheath 21 can also be arranged in the outer sheath 22 or there is no inner sheath arranged in the outer sheath. The guide wire 13 is of a slender and bendable flexible structure and includes a distal end and a proximal end. A joint 14 is further fixed at the proximal end of the outer sheath 22, and a joint 11 is fixed at the proximal end of the inner sheath 21. The guide wire 13 includes a distal end bent section 32, and the tip end part of the distal end bent section 32 is of a sharp tip structure.

The guide wire 13 is made of a high elastic material, the distal end bent section 32 is formed by bending the guide wire 13, and the structure thereof is a structure adapted to regain a preset bent shape from a straightened state. The cross section of the guide wire 13 is of a non-revolution body structure and can be non-revolution body structures such as a rectangle, a square, a triangle, an oval or the like. The internal structure of the inner sheath 21 is of a non-revolution body structure and can be non-revolution body structures such as a rectangle, a square, a triangle, an oval or the like. When the guide wire 13 is placed in the inner sheath 21, the cross section of the inner sheath 21 and the cross section of the guide wire 13 cannot be displaced. Preferably, the cross sections of the guide wire 13 and the inner sheath 21 have the same shape. Therefore, in a puncture process, the torsional freedom of the guide wire can be limited to some extent. Due to these cross sections of the guide wire 13 and the inner sheath, the guide wire 13 is easy to be orientated. Or, there is no inner sheath arranged in the outer sheath 22, and at this time, the internal structure of the outer sheath 22 is of a non-revolution body structure. The non-revolution body structure means that the shape of the cross section of the guide wire or the inner sheath is any geometrical shape except a revolution body structure. The revolution body herein means that two points are assumed at the two ends of an object, the two points are connected to form a line passing through the object, the line is used as the rotation center of the object, and each part of the object has the same shape when rotating to any position. Within a length range not larger than 3 mm beginning from the sharp tip end of the distal end of the guide wire, the rotation angle of the sharp tip end is at least 90 degree (i.e., on the length not larger than 3 mm of the sharp tip structure, the rotation angle of the sharp tip end relative to the proximal end of the sharp tip structure is at least 90 degree). After the sharp tip end rotates 90 degree, beginning from the proximal end of the sharp tip structure, the distal end bent section 32 can be in the shape of a spiral line, and the curvature radius thereof continuously increases, as shown in FIG. 7. When the pericardium puncture needle assembly is in use, the puncturing direction of the guide wire is located in a plane defined by the normal direction of the needle point plane of the outer sheath 22 and the axial line of the pipe body of the outer sheath. Preferably, the puncturing direction of the guide wire is in the normal direction of the needle point plane of the outer sheath 22.

In the implementations as shown in FIG. 8 and FIG. 9, the structures of the distal end bent section of the guide wire 13 are the same as those in the implementation as shown in FIG. 1. In the implementations as shown in FIG. 8 and FIG. 9, the rest of the structures of the outer sheath 22 are the same as the structures as shown in FIG. 2 to FIG. 6; and the structures of the joint 11 and the joint 14 can also be the same as those in the implementation as shown in FIG. 7.

Figure 10:
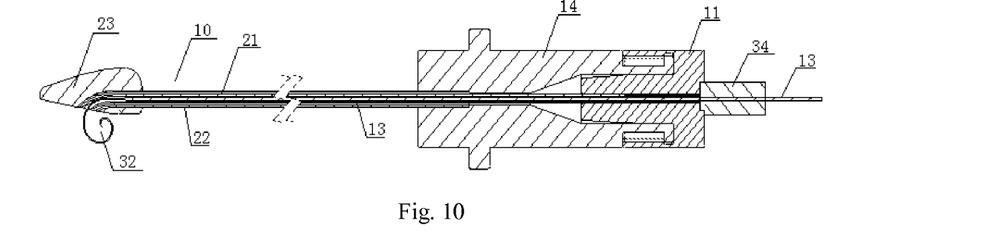
FIG. 10 is a schematic diagram of a structure of a pericardium puncture needle assembly 10 according to another implementation of the present invention.

FIG. 10 is a schematic diagram of a structure of a pericardium puncture needle assembly 10 according to another implementation of the present invention. As shown in FIG. 10, the pericardium puncture needle assembly 10 includes an outer sheath 22, and a guide wire 13 extends in the outer sheath 22. An inner sheath 21 can also be arranged in the outer sheath 22 or there is no inner sheath arranged in the outer sheath. When the inner sheath 21 is arranged, the guide wire 13 extends in the inner sheath 21. The guide wire 13 is of a slender and bendable flexible structure and includes a distal end and a proximal end. The guide wire 13 includes a distal end bent section 32, and the tip end part of the distal end bent section 32 is of a sharp tip structure. A joint 14 is further fixed at the proximal end of the outer sheath 22, and a joint 11 is fixed at the proximal end of the inner sheath 21.

The guide wire 13 is made of a high elastic material, the distal end bent section 32 is formed by bending the guide wire 13, and the structure thereof is a structure adapted to regain a preset bent shape from a straightened state. Within a length range not larger than 3 mm beginning from the sharp tip end of the distal end bent section of the guide wire, the rotation angle of the sharp tip end is at least 90 degree (i.e., on the length not larger than 3 mm of the sharp tip structure, the rotation angle of the sharp tip end relative to the proximal end of the sharp tip structure is at least 90 degree). After the sharp tip end rotates 90 degree, beginning from the proximal end of the sharp tip structure, the distal end bent section 32 can be in the shape of an involute, for example, a square involute, a triangular involute or others, and the curvature radius thereof continuously increases or increases step by step, as shown in FIG. 10. A guide wire positioner 34 is arranged at the proximal end of the guide wire 13, and the guide wire positioner 34 is of a removable structure and is clamped and fixed at the proximal end of the guide wire 13. A groove (not shown in the figure) is arranged on the proximal end of the joint 11, the shape of the distal end of the guide wire positioner 34 is matched with that of the groove, and thus the distal end can be inserted in the groove. The cross section of the guide wire positioner 34 is of a non-revolution body structure and can be non-revolution body structures such as a rectangle, a square, a triangle, an oval or the like. Therefore, in a puncture process, the torsional freedom of the guide wire can be limited to some extent.

In the implementation as shown in FIG. 10, the structures of the distal end bent section of the guide wire 13 are the same as those in the implementation as shown in FIG. 1. In the implementation as shown in FIG. 10, the rest of the structures of the outer sheath 22 are the same as the structures as shown in FIG. 2 to FIG. 6; and the structures of the joint 11 and the joint 14 can also be the same as those in the implementation as shown in FIG. 7.

Figure 11:
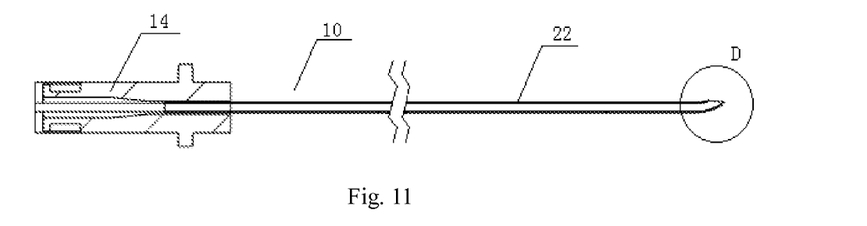
FIG. 11 is a schematic diagram of a structure of a pericardium puncture needle assembly according to another specific implementation of the present invention.
Figure 12:
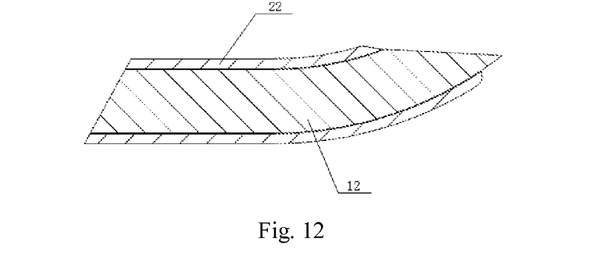
FIG. 12 is an enlarged view of D portion in FIG. 11.

FIG. 11 is a schematic diagram of a structure of a preferred pericardium puncture needle assembly 10 according to the present invention; and FIG. 12 is an enlarged view of D portion in FIG. 11. As shown in FIG. 11 and FIG. 12, the pericardium puncture needle assembly 10 includes a puncture needle 12 and an outer sheath 22, and the puncture needle 12 extends in the outer sheath 22. The distal end of the puncture needle 12 is of a structure with needle point for puncturing the thoracic wall. The distal end of the outer sheath 22 can further include a distal end bent section (not shown in the figure). The distal end of the outer sheath 22 is of a blunt end structure; namely, the surface of the distal end of the outer sheath 22 in contact with tissues is a smooth transition surface, in order to prevent all the tissues or organs in contact with the outer sheath 22 from being scratched. A joint 14 is fixed at the proximal end of the outer sheath 22, and the joint 14 can be a Luer joint.

Figure 13:
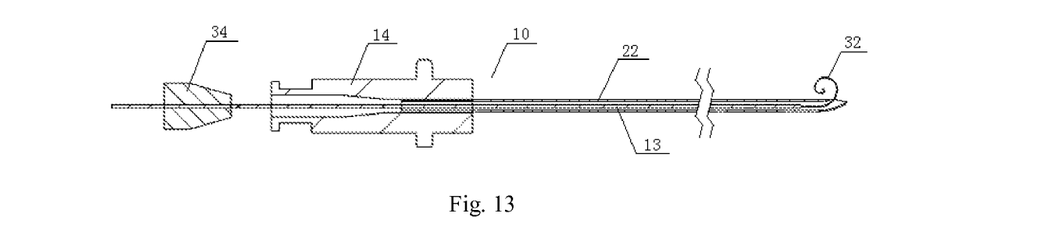
FIG. 13 is a sectional view of the pericardium puncture needle assembly shown in FIG. 11 and shows the internal structures of the pericardium puncture needle assembly of a preferred embodiment of the present invention.

FIG. 13 is a sectional view of the pericardium puncture needle assembly shown in FIG. 11 and shows the internal structure of the pericardium puncture needle assembly of a preferred embodiment of the present invention. When the distal end of the puncture needle 12 punctures the thoracic wall to enter the thoracic cavity, t the puncture needle is withdrawn from the outer sheath 22, and the guide wire 13 is propelled forwardly along the outer sheath 22.

The guide wire 13 extends in the outer sheath 22 and can freely slide in the outer sheath 22. The guide wire 13 is of a slender and bendable flexible structure and includes a distal end bent section 32; the distal end bent section 32 is formed by bending the guide wire 13, and the tip end part thereof is of a sharp tip structure. The guide wire 13 can be made of any proper high elastic material, for example, a nickel-titanium alloy material, and the distal end bent section 32 is adapted to regain a preset bent shape from a straightened state. A guide wire positioner 34 is fixed at the proximal end of the guide wire 13.

As shown in FIG. 13, after the sharp tip end rotates 90 degree, the bend of the distal end bent section 32 beginning from the proximal end of the sharp tip structure can be in the shape of a spiral line or an involute and can also be other proper irregular bends, for example, a combination of a circular arc and a straight line, a combination of an involute and a straight line or other proper bends.

The guide wire positioner 34 is removably fixed on the guide wire 13. When the guide wire is propelled forwardly, the guide wire positioner 34 is clamped and fixed at the proximal end of the joint 14, such that the rotation angle and the relative position of the guide wire 13 and the outer sheath 22 are fixed. Before the guide wire positioner 34 is fixed on the guide wire 13, the guide wire can be rotated and then fixed according to the demand on the puncturing direction. When the guide wire positioner 34 is clamped and fixed at the proximal end of the joint 14, an included angle α is formed between the plane where the axial line or the center line of the distal end bent section 32 of the guide wire is located and the normal direction of the end face of the distal end port of the outer sheath 22; preferably, the included angle α is 0 or 180 degree. When the guide wire positioner 34 is clamped and fixed at the proximal end of the joint 14, the sharp tip structure of the distal end of the guide wire extends to the outside of the sheath, in order to ensure the operation of puncture. After the guide wire positioner 34 is clamped and fixed at the proximal end of the joint 14 to adjust the rotation angle and the relative position of the guide wire 13 and the outer sheath 22, the guide wire positioner 34 can be removed to further insert the guide wire 13. As long as the rotation angle and the relative position of the guide wire 13 and the outer sheath 22 can be fixed to ensure the operation of puncture, the guide wire positioner 34 in the present invention can be of any proper structure or shape, which shall fall within the scope of the present invention.

According to a preferred embodiment of the present invention, when the pericardium puncture needle assembly is in use, the puncture needle 12 punctures the thoracic wall and enters into the thoracic cavity, the puncture needle is then withdrawn from the outer sheath 22, and the guide wire 13 is propelled forwardly along the outer sheath 22. When the distal end bent section 32 is entirely located in the puncture needle 12, the distal end bent section 32 is in the straightened state. When the guide wire 13 is propelled forwardly, the sharp tip end of the distal end bent section 32 extends out from the pipe body of the outer sheath 22. The sharp tip end punctures the pericardium, the guide wire 13 gradually enters the pericardium, the part of the distal end bent section 32 entered into the pericardium begins to gradually bend until regaining the preset shape, and the puncture is finished.

In the implementations as shown in FIG. 11 to FIG. 13, the rest of the structures of the guide wire 13 are the same as those in the implementation as shown in FIG. 1; and the rest of the structures of the puncture needle 12 are the same as those in the implementation as shown in FIG. 1. A negative pressure device can also be arranged at the proximal end of the pericardium puncture needle assembly 10, as described in the implementations as shown in FIG. 2 to FIG. 6.

Figure 14:
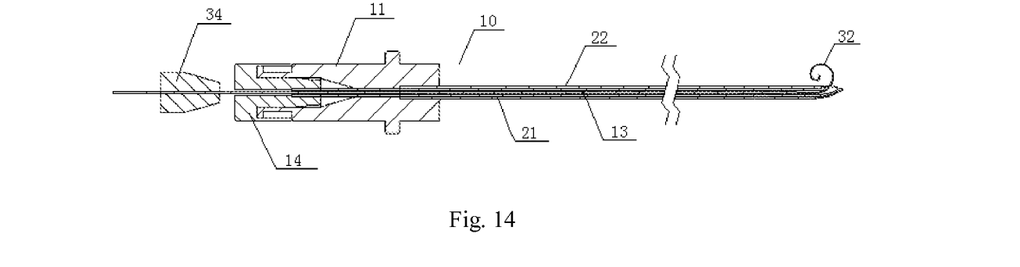
FIG. 14 is a schematic diagram of a structure of a pericardium puncture needle assembly according to another preferred embodiment of the present invention.

FIG. 14 is a schematic diagram of a structure of a pericardium puncture needle assembly according to another preferred embodiment of the present invention. As shown in FIG. 14, an inner sheath 21 is further arranged in the outer sheath 22, and the inner sheath 21 can freely slide in the outer sheath 22. When the inner sheath 21 is propelled forwardly to the distal end of the outer sheath 22, the distal end port of the outer sheath 22 and the distal end port of the inner sheath 21 are located in the same plane, so as to ensure that the distal ends of the outer sheath 22 and the inner sheath 21 do not hurt the pericardium when abutting the pericardium and ensure the operation of puncture. The outer sheath 22 is of a blunt end structure, and the inner sheath 21 can be of a blunt end structure or a non-blunt end structure. Due to the arrangement of the inner sheath 21, the inner diameter of the sheath is decreased, thus ensuring that the puncturing direction of the sharp tip end is vertical to the plane of the distal end port of the inner sheath 21 as much as possible in a puncture process of the guide wire 13. A joint 14 is fixed at the proximal end of the outer sheath 22, a joint 11 is fixed at the proximal end of the inner sheath 21, and the joint 11 and the joint 14 can be Luer joints.

After the distal end of the puncture needle 12 punctures the thoracic wall and enters into the thoracic cavity, the puncture needle is withdrawn from the outer sheath 22; the inner sheath 21 is conveyed into the outer sheath 22, and the guide wire 13 extends in the inner sheath 21; or the inner sheath 21 is conveyed into the outer sheath 22 at first, and then the guide wire 13 is propelled forwardly along the inner sheath 21. The guide wire 13 can freely slide in the inner sheath 21. The puncturing direction of the guide wire is in the plane where the distal end bent section 32 of the guide wire 13 is located. When the distal end bent section 32 is entirely located in the puncture needle 12, the distal end bent section 32 is in the straightened state. When the guide wire 13 is propelled forwardly, the sharp tip end of the distal end bent section 32 extends out from the pipe body of the inner sheath 21. The sharp tip end punctures the pericardium, the guide wire 13 gradually enters into the pericardium, the part of the distal end bent section 32 entered into the pericardium begins to gradually bend until regaining the preset shape, and the puncture is finished.

In the implementation as shown in FIG. 14, the rest of the structures are the same as those in the implementations as shown in FIG. 11 to FIG. 13.

Various components and structures described in the above implementations of the present invention can be mutually combined, as long as not conflicting with the original structures.

The embodiments of present invention are not limited to those embodiments described above. Without departing from the spirit and scopes of the present invention, various variations and improvements may be made to the invention in forms and details by those skilled in the art, all of which are regarded as falling into the protection scopes of the present invention.

The invention claimed is:

1. A pericardium puncture needle assembly, characterized in comprising a puncture needle and a guide wire, wherein the guide wire can slide in the puncture needle, and the guide wire is made of a high elastic material; the guide wire comprises a distal end bent section, the distal end bent section is formed by bending the guide wire and has a preset bent shape, and the distal end bent section is adapted to regain the preset bent shape from a straightened state, and a tip end part of the distal end bent section is of a sharp tip structure; the sharp tip structure is provided with a distal end and a proximal end, the distal end of the sharp tip structure is provided with a sharp tip end for puncturing, the rotation angle of the sharp tip end relative to the proximal end of the sharp tip structure is at least 90 degrees within a length not larger than 3 mm of the sharp tip structure; the puncturing direction of the guide wire is located in a plane defined by the normal direction of the needle point plane of the puncture needle and the axial line of the puncture needle, wherein the distal end of the puncture needle includes a distal end bent section.

2. The pericardium puncture needle assembly of claim 1, characterized in that the internal structure of the puncture needle is of a non-revolution body structure, and the guide wire is of a non-revolution body structure.

3. The pericardium puncture needle assembly of claim 1, characterized in that a guide wire positioner is provided at the proximal end of the guide wire, and the cross section of the guide wire positioner is of a non-revolution body structure.

4. The pericardium puncture needle assembly of claim 3, characterized in that the guide wire positioner is removably fixed on the guide wire; when the guide wire is propelled forwardly, the guide wire positioner is clamped and fixed at the proximal end of the outer sheath.

5. The pericardium puncture needle assembly of claim 4, characterized in that a joint is fixed at the proximal end of the puncture needle, the proximal end of the joint is provided with a groove matched with the shape of the distal end of the guide wire positioner, and the guide wire positioner can be clamped and fixed at the proximal end of the joint; after the guide wire positioner is clamped and fixed at the proximal end of the puncture needle, the sharp tip structure of the distal end of the guide wire extends to the outside of the puncture needle.

6. A pericardium puncture needle assembly, characterized in comprising an outer sheath and a guide wire, wherein the guide wire can slide in the outer sheath, and the guide wire is made of a high elastic material; the guide wire comprises a distal end bent section, the distal end bent section is formed by bending the guide wire and has a preset bent shape, and the distal end bent section is adapted to regain the preset bent shape from a straightened state, and a tip end part of the distal end bent section is of a sharp tip structure; the sharp tip structure is provided with a distal end and a proximal end, the distal end of the sharp tip structure is provided with a sharp tip end for puncturing, the rotation angle of the sharp tip end relative to the proximal end of the sharp tip structure is at least 90 degrees within a length not larger than 3 mm of the sharp tip structure; the puncturing direction of the guide wire is located in a plane defined by the normal direction of the needle point plane of the outer sheath and the axial line of the outer sheath, wherein
the guide wire comprises a proximal end bent section, and the proximal end of the outer sheath comprises a proximal bent section; or
the guide wire comprises a proximal end bent section, the outer sheath is further provided with an inner sheath, and the proximal end of the inner sheath comprises a proximal bent section.

7. The pericardium puncture needle assembly of claim 6, characterized in that the curvature radius of the proximal end bent section of the guide wire is selected such that within a length range of not larger than 20 mm, the rotation angle of the proximal end bent section of the guide wire is larger than 15 degree; the curvature radius of the proximal end bent section of the inner sheath is selected such that within a length range of not larger than 20 mm, the rotation angle of the proximal end bent section of the inner sheath is larger than 45 degree.

8. The pericardium puncture needle assembly of claim 7, characterized in that the normal direction of the needle point plane of the outer sheath and the axial line of the outer sheath define a plane A, the axial line or the center line of the proximal end bent section of the inner sheath is located in the same plane B, and an included angle α is formed between the plane A and the plane B; the axial line or the center line of the proximal end bent section of the guide wire is located in the same plane C, and an included angle β is formed between the plane C and a plane D where the axial line or the center line of the distal end bent section of the guide wire is located; the included angle β is equal to the included angle α.

9. The pericardium puncture needle assembly of claim 8, characterized in that both of the included angle α and the included angle β are 180 degree.

10. The pericardium puncture needle assembly of claim 6, characterized in that a guide wire positioner is provided at the proximal end of the guide wire, and the cross section of the guide wire positioner is of a non-revolution body structure.

11. The pericardium puncture needle assembly of claim 10, characterized in that the guide wire positioner is removably fixed on the guide wire; when the guide wire is propelled forwardly, the guide wire positioner is clamped and fixed at the proximal end of the outer sheath.

12. The pericardium puncture needle assembly of claim 11, characterized in that a joint is fixed at the proximal end of the outer sheath, the proximal end of the joint is provided with a groove matched with the shape of the distal end of the guide wire positioner, and the guide wire positioner can be clamped and fixed at the proximal end of the joint; after the guide wire positioner is clamped and fixed at the proximal end of the outer sheath, the sharp tip structure of the distal end of the guide wire extends to the outside of the outer sheath.

13. The pericardium puncture needle assembly of claim 11, characterized in that an included angle α is formed between the plane where the axial line or the center line of the distal end bend section of the guide wire is located and the normal direction of an end face of the distal end port of the outer sheath, wherein the included angle α is 0 or 180 degree.

14. The pericardium puncture needle assembly of claim 6, characterized in that the outer sheath is further provided with an inner sheath, the inner sheath can freely slide in the outer sheath, and the guide wire extends in the inner sheath; an end face of the distal end port of the inner sheath and an end face of the distal end port of the outer sheath are located in the same plane; and the distal end of the outer sheath is of a blunt end structure.

15. The pericardium puncture needle assembly of claim 6, characterized in that the distal end of the outer sheath includes a distal end bent section.

16. A pericardium puncture needle assembly, characterized in comprising an outer sheath, a puncture needle and a guide wire, wherein the puncture needle can slide in the outer sheath, and when the puncture needle is pulled out of the outer sheath, the guide wire can slide in the outer sheath, and the guide wire is made of a high elastic material; the guide wire comprises a distal end bent section, the distal end bent section is formed by bending the guide wire and has a preset bent shape, and the distal end bent section is adapted to regain the preset bent shape from a straightened state, and a tip end part of the distal end bent section is of a sharp tip structure; the sharp tip structure is provided with a distal end and a proximal end, the distal end of the sharp tip structure is provided with a sharp tip end for puncturing, the rotation angle of the sharp tip end relative to the proximal end of the sharp tip structure is at least 90 degrees within a length not larger than 3 mm of the sharp tip structure; the puncturing direction of the guide wire is located in a plane defined by the normal direction of the needle point plane of the outer sheath and the axial line of the outer sheath, wherein the guide wire comprises a proximal end bent section, and the proximal end of the outer sheath comprises a proximal bent section; or the guide wire comprises a proximal end bent section, the outer sheath is further provided with an inner sheath, and the proximal end of the inner sheath comprises a proximal bent section.

17. The pericardium puncture needle assembly of claim 16, characterized in that the curvature radius of the proximal end bent section of the guide wire is selected such that within a length range of not larger than 20 mm, the rotation angle of the proximal end bent section of the guide wire is larger than 15 degree; the curvature radius of the proximal end bent section of the inner sheath is selected such that within a length range of not larger than 20 mm, the rotation angle of the proximal end bent section of the inner sheath is larger than 45 degree.

18. The pericardium puncture needle assembly of claim 17, characterized in that the normal direction of the needle point plane of the outer sheath and the axial line of the outer sheath define a plane A, the axial line or the center line of the proximal end bent section of the inner sheath is located in the same plane B, and an included angle α is formed between the plane A and the plane B; the axial line or the center line of the proximal end bent section of the guide wire is located in the same plane C, and an included angle β is formed between the plane C and a plane D where the axial line or the center line of the distal end bent section of the guide wire is located; the included angle β is equal to the included angle α.

19. The pericardium puncture needle assembly of claim 18, characterized in that both of the included angle α and the included angle β are 180 degree.

20. The pericardium puncture needle assembly of claim 16, characterized in that the internal structure of the puncture needle is of a non-revolution body structure, and the guide wire is of a non-revolution body structure.

21. The pericardium puncture needle assembly of claim 16, characterized in that a guide wire positioner is provided at the proximal end of the guide wire, and the cross section of the guide wire positioner is of a non-revolution body structure.

22. The pericardium puncture needle assembly of claim 21, characterized in that the guide wire positioner is removably fixed on the guide wire; when the guide wire is propelled forwardly, the guide wire positioner is clamped and fixed at the proximal end of the outer sheath.

23. The pericardium puncture needle assembly of claim 22, characterized in that a joint is fixed at the proximal end of the outer sheath, the proximal end of the joint is provided with a groove matched with the shape of the distal end of the guide wire positioner, and the guide wire positioner can be clamped and fixed at the proximal end of the joint; after the guide wire positioner is clamped and fixed at the proximal end of the outer sheath, the sharp tip structure of the distal end of the guide wire extends to the outside of the outer sheath.

24. The pericardium puncture needle assembly of claim 22, characterized in that an included angle α is formed between the plane where the axial line or the center line of the distal end bend section of the guide wire is located and the normal direction of an end face of the distal end port of the outer sheath, wherein the included angle α is 0 or 180 degree.

25. The pericardium puncture needle assembly of claim 16, characterized in that the outer sheath is further provided with an inner sheath, the inner-sheath can freely slide in the outer sheath, and the guide wire extends in the inner sheath; an end face of the distal end port of the inner sheath and an end face of the distal end port of the outer sheath are located in the same plane; and the distal end of the outer sheath is of a blunt end structure.

26. The pericardium puncture needle assembly of claim 16, characterized in that the distal end of the outer sheath includes a distal end bent section.

* * * * *